United States Patent [19]

Lantzsch et al.

[11] Patent Number: 5,639,713
[45] Date of Patent: Jun. 17, 1997

[54] HERBICIDAL COMPOSITIONS BASED ON N-(4-FLUORO-PHENYL)-N-ISOPROPYL-CHLOROACETAMIDE, AND PROCESS FOR THE PREPARATION OF THIS COMPOUND

[75] Inventors: Reinhard Lantzsch, Wuppertal; Heinz Förster, Kadenbach; Thomas Schmidt, Haan; Karl Steinbeck, Burscheid; Markus Dollinger; Hans-Joachim Santel, both of Leverkusen, all of Germany

[73] Assignee: Bayer Aktiengesellschaft, Leverkusen, Germany

[21] Appl. No.: 544,751

[22] Filed: Oct. 18, 1995

[30] Foreign Application Priority Data

Oct. 25, 1994 [DE] Germany .................. 44 38 001.1

[51] Int. Cl.$^6$ .................................... A01N 37/22
[52] U.S. Cl. .................................................. 504/342
[58] Field of Search .................................... 504/342

[56] References Cited

U.S. PATENT DOCUMENTS

| Re. 26,961 | 10/1970 | Hamm et al. | 71/118 |
|---|---|---|---|
| 3,960,948 | 6/1976 | Shackleton et al. | 260/562 B |
| 4,021,483 | 5/1977 | Lutz et al. | 260/562 B |
| 4,140,774 | 2/1979 | Salbeck et al. | 424/411 |
| 4,418,021 | 11/1983 | Patel | 260/943 |
| 4,453,965 | 6/1984 | Patel | 71/87 |

FOREIGN PATENT DOCUMENTS

| 736779 | 1/1970 | Belgium . |
|---|---|---|
| 2318861 | 2/1977 | France . |
| 2027822 | 12/1970 | Germany . |
| 2633159 | 1/1978 | Germany . |
| 63-126847 | 5/1988 | Japan . |
| 1269692 | 4/1972 | United Kingdom . |
| 1316782 | 5/1973 | United Kingdom . |

OTHER PUBLICATIONS

E. Müller, "Methoden der Organischen Chemie", vol. XI/32, p. 13, Georg Thieme Verlag, Stuttgart, (1958).
Chemical Abstracts of Japan, vol. 12, No. 365, abstract of JP 63–119,447, (1988).
Oyama et al, C.A., vol. 109, (1988) 109:210673s.

Primary Examiner—Allen J. Robinson
Attorney, Agent, or Firm—Sprung Horn Kramer & Woods

[57] ABSTRACT

The invention relates to the use of the compound N-(4-fluoro-phenyl)-N-isopropylchloroacetamide of the formula (I)

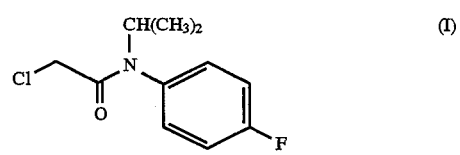

which is known, as active compound in selective herbicidal compositions, for example for combating weeds in maize cultures, and to a new process for the preparation of this active compound.

The compound (I) is obtained in very high yields by reacting N-isopropyl-4-fluoro-aniline with approximately equimolar amounts of chloroacetyl chloride at temperatures between 20° and 150° C. in the presence of an inert diluent, such as, for example, toluene, without addition of an acid binder.

3 Claims, No Drawings

HERBICIDAL COMPOSITIONS BASED ON N-(4-FLUORO-PHENYL)-N-ISOPROPYL-CHLOROACETAMIDE, AND PROCESS FOR THE PREPARATION OF THIS COMPOUND

The invention relates to the use of the compound N-(4-fluoro-phenyl)-N-isopropylchloroacetamide, which is known, as active compound in selective herbicidal compositions and to a new process for the preparation of this compound.

N-(4-Fluoro-phenyl)-N-isopropyl-chloroacetamide has already been disclosed as an intermediate for agrochemicals (cf. DE-OS (German Published Specification) 2633159, U.S. Pat. No. 4,140,774, U.S. Pat. No. 4,418,021). However, the use of the abovementioned compound as a herbicide has not been disclosed to date.

It has now been found that the compound N-(4-fluoro-phenyl)-N-isopropyl-chloroacetamide of the formula (I) below

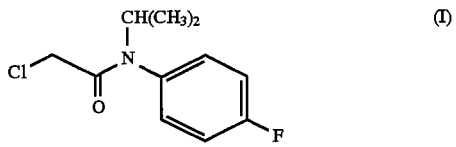

is highly suitable for the selective combating of weeds in important cultures.

To date, the reaction of N-isopropyl-4-fluoro-aniline with chloroacetyl chloride in the presence of pyridine (cf. U.S. Pat. No. 4,453,965) has been disclosed as a process for the preparation of the compound of the formula (I). However, the recovery of pyridine from the pyridine hydrochloride formed in this reaction is very complicated to carry out on an industrial scale.

It has furthermore been disclosed that the compound N-(isopropyl-phenyl)-chloroacetamide, which is similar, can be prepared by reacting N-isopropyl-aniline with chloroacetic acid and phosphoryl chloride or phosphorus trichloride (cf. U.S. Pat. No. 3,960,948). However, the yields in this process are not entirely satisfactory, and phosphorus-containing wastewater has to be disposed of by means of phosphate precipitation.

It has now been found that the compound of the formula (I) is obtained in very high yields when N-isopropyl-4-fluoro-aniline is reacted with approximately equimolar mounts of chloroacetyl chloride at temperatures between 20° C. and 150° C. in the presence of an inert diluent, such as, for example, toluene, without addition of an acid binder.

This procedure results in no wastewater, and the hydrogen chloride which is liberated can be reused for other purposes.

The course of the reaction in the synthesis of the compound of the formula (I) can be outlined by the following equation:

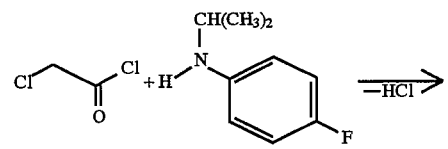

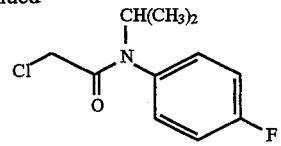

The starting substances required for the preparation of the compound of the formula (I) are known chemicals.

The compound of the formula (I) can be used in defoliants, desiccants, agents for destroying broad-leaved plants and, especially, as weed-killers. By weeds, in the broadest sense, there are to be understood all plants which grow in locations where they are undesired.

The compound of the formula (I) can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the compound of the formula (I) is in no way restricted to these genera, but also extends in the same manner to other plants.

The compound of the formula (I) is suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The compound of the formula (I) according to the invention is particularly suitable for selectively combating monocotyledon and dicotyledon weeds in monocotyledon cultures, such as, for example, in maize, especially by the pre-emergence method.

The compound of the formula (I) can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 per cent by weight of active compound, preferably between 0.5 and 90%.

For combating weeds, the compound of the formula (I) according to the invention, as such or in the form of their formulations, can also be used as mixtures with known herbicides, finished formulations or tank mixes being possible.

Suitable herbicies for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuronethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The compound of the formula (I) can be used as such, in the form of its formulations or in the use forms prepared therefrom by further dilution, such as ready-to-use solutions, suspensions, emulsions, powders, pastes and granules. They are used in the customary manner, for example by watering, spraying, atomizing or scattering.

The compound of the formula (I) can be applied either before or after emergence of the plants. It can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the compound of the formula (I) can be seen from the following examples.

PREPARATION EXAMPLE

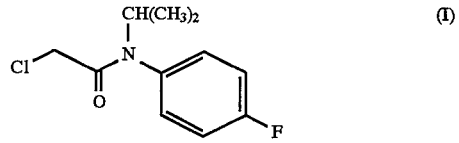

15.3 g (0.1 mol) of 4-fluoro-N-isopropyl-aniline are dissolved in 100 ml of toluene, and 11.3 g (0.1 mol) of chloroacetyl chloride are added dropwise at 60° C. to the stirred solution. The mixture is then heated at the boil for 90 minutes; then, after the mixture has cooled slightly, the solvent is carefully removed by distillation under a water pump vacuum and finally under an oil-pump vacuum.

22.9 g (96.5% of theory) of N-(4-fluoro-phenyl)-N-isopropyl-chloroacetamide are obtained as a clear liquid residue of refractive index 1.5210.

USE EXAMPLE

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control.

The figures denote:

0%=no action (like untreated control)

100% =total destruction

In this test, a potent herbicidal action (cf. Table A) is shown by the compound of the formula (I) combined with a very good tolerance by crop plants, such as, for example, maize.

TABLE A

| Application rate | Pre-emergence test/greenhouse | | | | | |
|---|---|---|---|---|---|---|
| | Maize | Cynodon | Echinochloa | Setaria | Amaranthus | Galinsoga |
| 1000 g/ha (I) | 0 | 100 | 100 | 100 | 90 | 95 |

We claim:

1. A herbicidal composition comprising a herbicidally effective amount of the compound N-(4-fluorophenyl)-N-isopropyl-chloroacetamide, which has the formula (I):

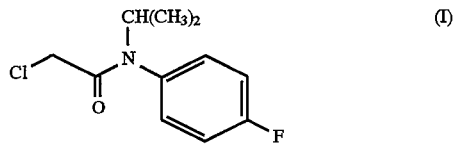

in admixture with an extender and a surface active agent.

2. A process for preparing the herbicidal composition according to claim 1, which comprises mixing a herbicidally effective amount of the compound N-(4-fluorophenyl)-N-isopropyl-chloroacetamide with an extender and a surface active agent.

3. A method of combating weeds comprising applying a herbicidally effective amount of the compound N-(4-fluorophenyl)-N-isopropyl-chloroacetamide to the weeds, their environment or to a place from which it is desired to exclude such weeds.

* * * * *